United States Patent [19]

Cooper et al.

[11] Patent Number: 4,727,416
[45] Date of Patent: Feb. 23, 1988

[54] ELECTRONIC VIDEO DENTAL CAMERA

[75] Inventors: David H. Cooper, Saratoga; Charles S. Bush, Los Gatos, both of Calif.

[73] Assignee: Fuji Optical Systems, Inc., Los Gatos, Calif.

[21] Appl. No.: 22,171

[22] Filed: Mar. 5, 1987

[51] Int. Cl.$^4$ .......................... H04N 7/18; A61B 1/04; A61B 1/06
[52] U.S. Cl. .......................................... 358/98; 128/6; 358/229; 378/99; 433/29
[58] Field of Search .................... 358/98, 225, 229; 433/29, 30, 31; 128/6; 378/99, 100

[56] References Cited

U.S. PATENT DOCUMENTS

| | | | |
|---|---|---|---|
| 3,622,785 | 11/1971 | Irwin | 378/99 |
| 3,884,222 | 5/1975 | Moore | 433/31 |
| 4,260,376 | 4/1981 | Litel | 433/29 |
| 4,468,197 | 8/1984 | Provost | 433/30 |
| 4,479,499 | 10/1984 | Alfano | 433/29 |
| 4,629,425 | 12/1986 | Detsch | 433/29 |
| 4,667,229 | 5/1987 | Cooper | 358/98 |

Primary Examiner—Howard Britton
Attorney, Agent, or Firm—Steven F. Caserza

[57] ABSTRACT

An electronic video dental camera is provided having a general shape of prior art dental mirrors, thereby being readily manipulated by dentists who are universally familiar with the manipulation of prior art dental mirrors. Such an electronic video dental camera includes a handle to be held the user, and a camera head located at the distal end of the handle, with the camera head being formed at an angle to the handle. One embodiment also includes a mirror so that the dental camera can be used simultaneously as both a video dental camera and a dental mirror. Another embodiment includes means to cause, as desired, the flow of a selected fluid over the camera lens in order to defog and/or clean the camera lens, thereby allowing proper viewing. In one embodiment, the camera head also includes light sources for properly illuminating the area to be viewed. As a feature of one embodiment, the handle includes means for transporting all appropriate signals and fluids to and from the camera head, and, if desired, valves and switching means located on the handle for controlling such communication to the camera head. In one embodiment, the handle is uniquely designed to have a one piece connector to connect to a cable from video monitor and control equipment, such connector providing communication with all elements connected to the camera head, such as power for a light source, video signals, fluids, etc.

28 Claims, 5 Drawing Figures

ELECTRONIC VIDEO DENTAL CAMERA

BACKGROUND

This invention is an electronic video dental camera having a handle and head shaped in the general form of a dental mirror, for use in placement in a dental patient's mouth and allowing areas within the mouth be displayed via a video signal.

For years, dentists have used dental mirrors for insertion in a dental patient's mouth for reflecting images of areas within the patient's mouth for viewing by the dentist. This technique works, although it has several disadvantages. First, it is often difficult to hold the dental mirror in an appropriate position in order to reflect the desired image. Secondly, it is more difficult to ensure that proper lighting is available to the area within the mouth to be reflected by the dental mirror. An even greater disadvantage is that it is very difficult to use such prior art dental mirrors in a situation where a dentist wishes to discuss certain regions within the mouth with other people, be it the patient, colleagues, dental assistants, or students in a teaching institution.

Electronic video endoscopes have been used in recent years, for example as is described in U.S. patent application Ser. No. 611,684 filed May 18, 1984 (now U.S. Pat. No. 4,667,229) on an invention of Cooper et al, which is hereby incorporated by reference. Such prior art video endoscopes use either fiber optics or a miniature camera, such as a charge coupled device (CCD), in order to transport an image to a monitor. Such prior art video endoscopes come in a variety of sizes, but are typically rather small and tubular in nature in order that they maybe easily inserted within a body cavity or surgical opening. Certain prior art endoscopes include a light source located at their end in order to ensure proper lighting is available for transporting the image to the monitor.

However, such prior art video endoscopes were not specifically designed for use in dental applications and are rather clumsy in such applications. As one example, it is very difficult, if not impossible, to properly view the lingual aspects of the teeth using such prior art video endoscopes, due to their tubular shape.

SUMMARY

In accordance with the teachings of this invention, an electronic video dental camera is provided which overcomes the disadvantages of both prior art dental mirrors, endoscopes, and video endoscopes. In accordance with the teachings of this invention, an electronic video dental camera is provided having a general shape of prior art dental mirrors, thereby being readily manipulated by dentists who are universally familiar with the manipulation of prior art dental mirrors. Such an electronic video dental camera includes a handle to be held the user, and a camera head located at the distal end of the handle, with the camera head being formed at an angle to the handle, as in prior art dental mirrors. In one embodiment the dental camera constructed in accordance with the teachings of this invention also includes a mirror so that the dental camera can be used simultaneously as both a video dental camera and a dental mirror. In another embodiment, means are provided to cause, as desired, the flow of a selected fluid over the camera lens in order to defog and/or clean the camera lens, thereby allowing proper viewing. In one embodiment, the camera head also includes light sources for properly illuminating the area to be viewed. As a feature of one embodiment of this invention, the handle of the dental camera includes means for transporting all appropriate signals and fluids to and from the camera head, and, if desired, valves and switching means located on the handle for controlling such communication to the camera head.

In one embodiment of this invention, the handle is uniquely designed to have a one piece connector to connect to a cable from video monitor and control equipment, such connector providing communication with all elements connected to the camera head, such as power for a light source, video signals, fluids, etc.

DETAILED DESCRIPTION

Figure 1:
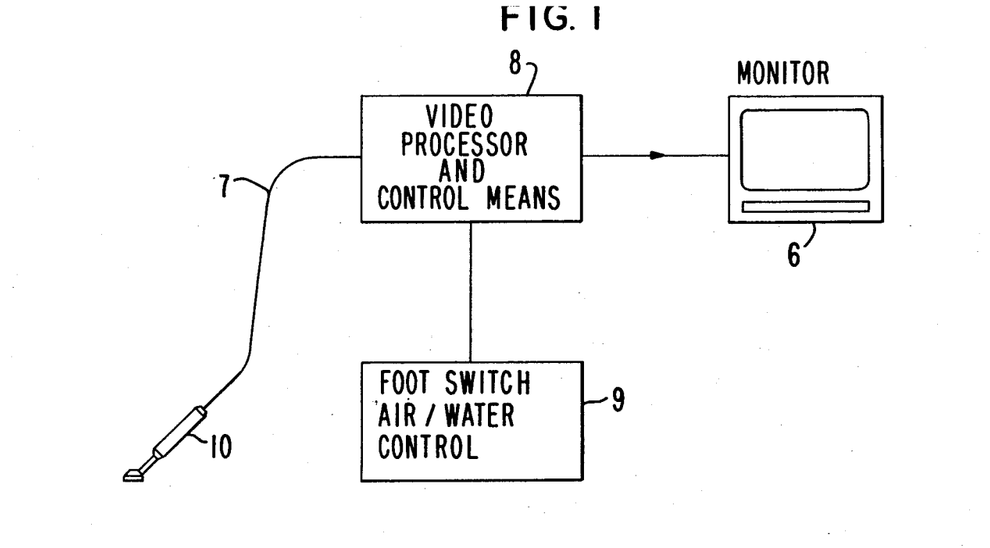
FIG. 1 is a diagram depicting the use of an electronic video camera constructed in accordance with the teachings of this invention.

FIG. 1 shows the use of a dental camera 10 constructed in accordance with the teachings of this invention. Video processor and control means 8 serves to provide power, light, and if desired fluid and other appropriate signals via cable 7 to dental camera 10. Video processor and control means 8 provides a video signal to video monitor 6 in order that users may view a location within a patient's mouth by way of dental camera 10. If desired, foot switch 9 is used to provide a signal to video processor and control means 8 indicating when air and/or fluids are to be sent by video processor and control means 8 to dental camera 10.

Figure 2:
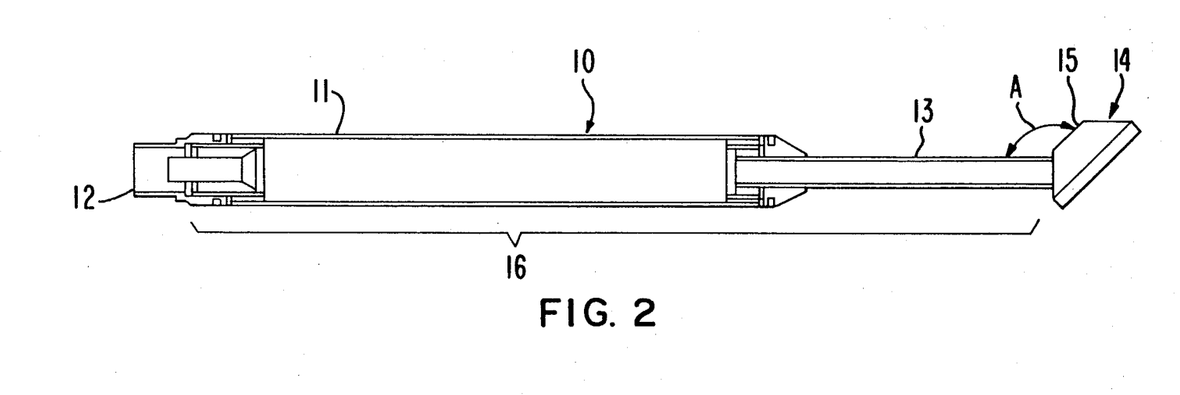
FIG. 2 is a cross sectional view of one embodiment of a video dental camera constructed in accordance with the teachings of this invention.

FIG. 2 shows a cross section of one embodiment of a video dental camera constructed in accordance with the teachings of this invention. Video dental camera 10 includes body 16 having handle 11 suitable for being held by an operator, and, if desired having forward extension 13. At one end of handle 11 is located connector 12 for connection, via a cable assembly (not shown) to video processor and control unit 8 (FIG. 1). If desired, forward extension 13 and handle 11 have generally circular cross section, although other suitable shapes, such as octagonol, and polygonal can be used. The important point is that handle 11 should be easily and comfortably griped by the user, and forward extension 13 should be of a general size and cross section which is convenient for insertion into the patient's mouth and, of course, comfortable for the patient. In one embodiment of this invention, forward extension 13 or handle 11 is malleable, or dental camera 10 includes suitable joints and/or pivots such that its shape can be changed any number of times for selected purposes.

Located at the distal end of forward extension 13, and mounted on forward extension 13 at an angle A to forward extension 13, is camera head 14. Face 15 of camera head 14 includes means for receiving an image within a patient's mouth to be displayed on a video monitor. In one embodiment of this invention, such means for receiving the image is fiber optic tubes or one or more rod lens assemblies or a combination thereof with or without additional lenses, which transmit the image to an image sensor (not shown) either within forward extension 13, body 16 or, in another embodiment of this invention, the image is transmitted by one or more rod lens assemblies or fiber optic cable, or a combination thereof with or without additional lenses, through connector 12 to an image sensor located in external video equipment (not shown). However, in a preferred embodiment the image sensor is located directly in camera head 14 and receives the image from the patient s mouth via a lens, without the need for fiber optics.

Figure 3:
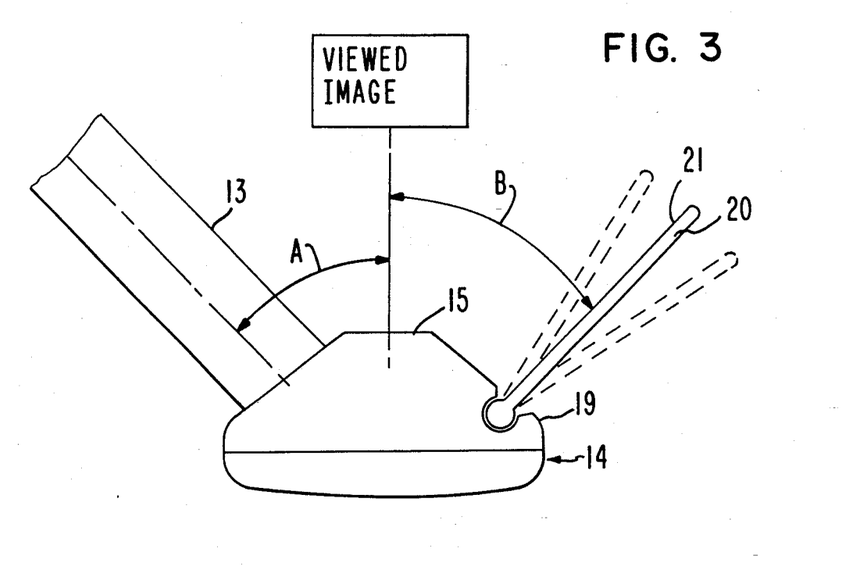
FIG. 3 is a more detailed view of the forward extension, camera head, and mirror attachment of one of embodiment of a dental camera constructed in accordance with the teachings of this invention.

In one embodiment of this invention, as shown in FIG. 3, a mirror 20 having a reflecting face 21 is placed such that the operator can use mirror 20 in much the same manner as prior art dental mirrors are used in order to visually see the viewed image which is simultaneously being received by camera head 14. While FIG. 3 shows one embodiment of mirror 20 which is a placed in a groove 19 inside of camera head 15, in another embodiment (not shown) mirror 20 is affixed to opposite sides to camera head 14. In the embodiment shown FIG. 3, mirror is held in a slot having a circular cross section within camera head 15 in an interference fit, and thus angle B is adjustable. To allow for such adjustment, the opening into camera head 14 is wider than the thickness of mirror 20. Mirror 20 is placed at an angle B to the viewed image. A wide range of camera head to viewed image angle A and mirror to viewed image angle B can be used in accordance with the teachings of this invention, however it has been found that an angle A of approximately 45° is roughly equivalent to typical prior art dental mirrors. Similarly, a dental mirror angle B of approximately 45° is suitable for most uses. However, angles A and B can vary widely, and there is no required relationships between angles A and B, so long as the dental camera and mirror 20 function in an convenient manner for the operator. In fact, angle A can range from 0° to 180°, and angle B can range from 0° to 180° without detracting from the spirit of this invention. Furthermore, it possible that camera head 14 be inverted such that face 15 is located on the bottom of FIG. 3, with of course a different location for the viewed image. In another embodiment of this invention, a face of camera head 14 is itself used as a mirror.

Figure 4:
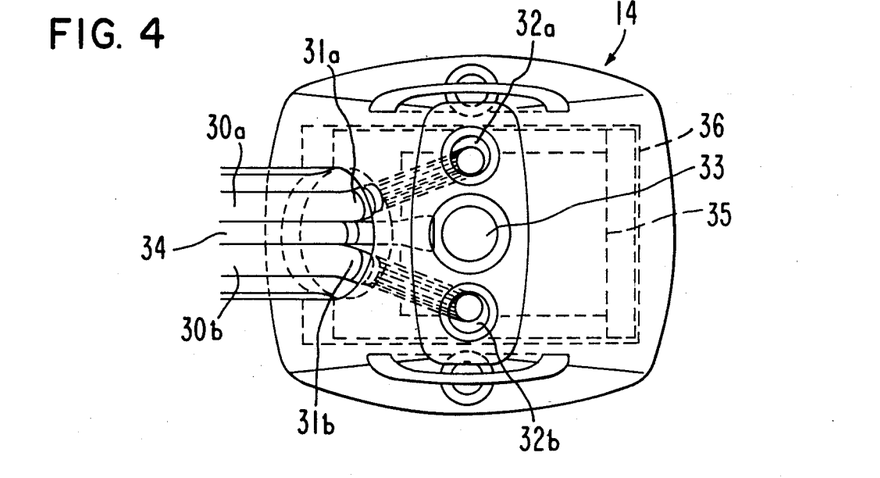
FIG. 4 is a plan view of one embodiment of a camera head constructed in accordance with the teachings of this invention.

FIG. 4 shows a cross sectional phantom view of camera head 14. In this embodiment, fiber optic light guides 30a and 30b are used to receive light from a light source (not shown) which may comprise, for example a halogen lamp or a Xenon arc lamp located at the proximal end of light guides 30a and 30b, and conduct this light through fiber optic curvatures 31a and 31b to illumination lenses 32a and 32b respectively. Also shown in FIG. 4 is image lens 33 and image sensor 35 which is mounted on hybrid assembly substrate 36 located within cavity 37. As shown in FIG. 4, in one embodiment of this invention, the center of the ends of fiber optic light pipes 30a and 30b are offset from the center of illumination lenses 32a and 32b, respectively, in a direction toward image lens 33. This causes the light being emitted from fiber optic light pipes 30a and 30b to be directed toward the image being viewed. Also, in one embodiment of this invention, illumination lenses 32a and 32b are dispersion lenses which include a "frosting" to disperse the light. Image sensor 35 is connected to video control cable 34 which communicates power and control signals to image sensor 35 and communicates video signals to the video processor and control means 8 of FIG. 1. As an alternative embodiment, a third fiber optic cable or a rod lens assembly (not shown) is used to conduct the image from image lens 33 to an image sensor located in forward extension 13, handle 11, or via connector 12 (FIG. 2) to an image sensor located external to dental camera 10.

Figure 5:
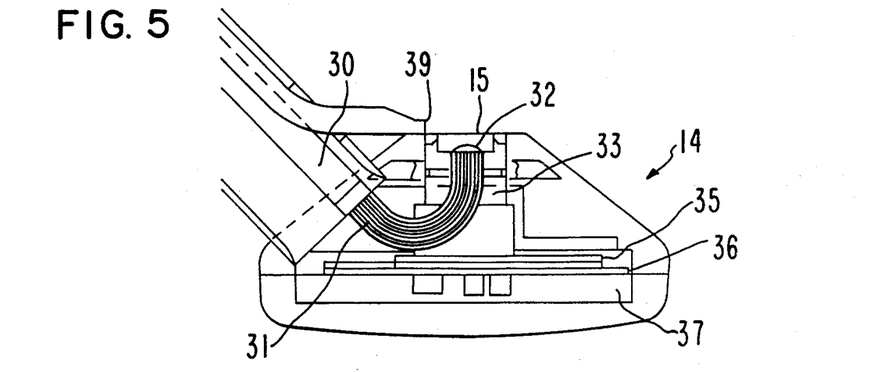
FIG. 5 is a cross sectional view of one embodiment of a camera head constructed in accordance with the teachings of this invention.

FIG. 5 shows a cross sectional phantom view of the structure shown in FIG. 3, with elements numbered in a similar fashion. Thus, shown in FIG. 5 are fiber optic light guide 30, fiber optic curvature 31, and illumination lens 32. In one embodiment, illumination lens 32 is a dispersion lens which serves to properly distribute the light over a wider angle and area upon exit from fiber optic light guide 30, to correspond to the field of view of image lens 33. FIG. 5 also shows image lens 33 located within camera head 14 between camera head face 15 and image sensor 35. In the embodiment shown in FIG. 5, image lens 33 is affixed directly to image sensor 35. In an alternative embodiment of this invention, image lens 33 is affixed to the body of camera head 14, and image sensor 35 is also affixed, via substrate 36, to the body of camera head 14, thereby maintaining image lens 33 and image device 35 in fixed relationship. In another embodiment of this invention, fiber optic curvature 31 is not used, but is replaced by a prism or mirror assembly which serves to reflect light from fiber optic light guide 30 to face 15 of camera head 14. If desired, a suitable lens can be placed on the fiber optic side of the prism or mirror, or on the face 15 side of the prism or mirror, or in both locations if desired.

In one embodiment of this invention an infrared filter is place between the light source (not shown) and fiber optic light guide 30. This infrared filter serves to prevent damage to fiber optic light guide 30 by masking out damaging infrared rays from the light source. In another embodiment of this invention, color filters are used as desired. For example, cplor filters can be placed anywhere between the light source and illumination lens 32 in order to selectively apply desired colors of illumination to the image being viewed. Alternatively, one or more color filters can be placed between image lens 33 and image sensor 35, again in order to selectively remove desired colors of the image being presented to image sensor 35. In yet another embodiment, an infrared blocking filter is placed in the image path between the image being viewed and image sensor 35 in order to prevent infrared energy from being applied to image sensor 35. This is particularly useful, for example, when a dentist is using a laser to perform certain dental procedures during which time a relatively larger amount of infrared energy is present. If not blocked out, this infrared energy would be detected by image sensor 35, resulting in a "washed out" video signal.

In one embodiment of this invention, forward extension 13 includes fluid jet 39 (FIG. 5) which serves to allow fluid to be introduce across face 15 of camera head 14. In this manner, for example, a constant or pulsed flow of gas, such as air, can be made to provide a laminar flow across image lens 33 to prevent fogging. If desired, a liquid such as water can be introduced as well in order to clean image lens 33. Fluid jet 39 can also be placed in any convenient location.

The specific embodiments of this invention described in this specification are intended to serve by way of example and are not a limitation on the scope of my invention. Numerous other embodiments of this invention will become apparent to those of ordinary skill in the art in light of the teachings of this specification.

We claim:

1. A dental camera for use in displaying an image from inside the mouth onto a monitor comprising an electronic video endoscope having a shape like a dental mirror, said endoscope comprising:
   a handle;
   a camera head including a camera lens located at the distal end of said handle, said camera head being formed such that said camera lens is placed at an angle from the axis of said handle; and
   means for providing a flow of fluid over the surface of said camera lens.

2. A dental camera as in claim 1 wherein said fluid is selected from the group of fluids consisting of gas, liquid, slurry, and mixtures of gas, liquid and slurry.

3. A dental camera as in claim 1 wherein said handle further comprises valve means for controlling said fluid.

4. A dental camera as in claim 1 wherein said handle includes a break point allowing at least said camera head to be removed.

5. A dental camera as in claim 1 which includes a malleable member connecting said handle and said camera head.

6. A dental camera as in claim 1 wherein said handle comprises means interior to said handle, for communication with said camera head.

7. A dental camera as in claim 6 which comprises means to connect one or more cables to said distal end of said handle for communication between said camera head and external devices.

8. A dental camera as in claim 6 wherein said communication with said camera head comprises items selected from the set of items consisting of gas, liquid, slurry, light, electrical power, and electrical signals.

9. A dental camera as in claim 8 wherein said handle further comprises control means for controlling said items.

10. A dental camera as in claim 1 wherein said camera head comprises an imaging device.

11. A dental camera as in claim 10 wherein said imaging device is a CCD.

12. A dental camera as in claim 10 wherein said camera lens is affixed to said imaging device.

13. A dental camera as in claim 10 wherein said camera lens is affixed to said camera head, and said imaging device is affixed to said camera head.

14. A dental camera for use in displaying an image from inside the mouth onto a monitor comprising an electronic video endoscope having a shape like a dental mirror, said endoscope comprising:
   a handle; and
   a camera head including a camera lens located at the distal end of said handle, said camera head being formed such that said camera lens is placed at an angle from the axis of said handle;
   wherein said camera head includes means for providing light and a lens such that the light from said means for providing light is dispersed toward the area being viewed by said camera head.

15. A dental camera as in claim 14 wherein said means for providing light comprises means for reflecting light within said camera head in order to exit said camera head and illuminate a desired field of view.

16. A dental camera as in claim 14 which includes a malleable member connecting said handle and said camera head.

17. A dental camera as in claim 14 which further includes one or more color filters in the path between said means for providing light and an image being viewed.

18. A dental camera as in claim 17 wherein said color filter is an infrared filter.

19. A dental camera as in claim 14 wherein said means for providing light comprises a fiber optic light guide bringing illumination from a light source.

20. A dental camera as in claim 19 wherein said fiber optic light guide includes a bend within the range of 0°–180°.

21. A dental camera as in claim 20 wherein said bend is approximately 135°.

22. A dental camera for use in displaying an image from inside the mouth onto a monitor comprising an electronic video endoscope having a shape like a dental mirror, said endoscope comprising:
   a handle;
   a camera head including a camera lens located at the distal end of said handle, said camera head being formed such that said camera lens is placed at an angle from the axis of said handle;
   an imaging device; and
   a color filter in the image path between the image being viewed and said imaging device.

23. A dental camera as in claim 22 wherein said color filter is an infrared filter.

24. A dental camera as in claim 22 which includes a malleable member connecting said handle and said camera head.

25. A dental camera for use in displaying an image from inside the mouth onto a monitor comprising an electronic video endoscope having a shape like a dental mirror, said endoscope comprising:
   a handle;
   a camera head including a camera lens located at the distal end of said handle, said camera head being formed such that said camera lens is placed at an angle from the axis of said handle; and
   an imaging means located external to said camera head.

26. A dental camera as in claim 25 wherein said imaging device is located within said handle.

27. A dental camera as in claim 25 wherein said imaging device is located external to said handle.

28. A dental camera as in claim 25 which includes a malleable member connecting said handle and said camera head.

* * * * *

REEXAMINATION CERTIFICATE (1969th)

United States Patent [19]

Cooper et al.

[11] B1 4,727,416

[45] Certificate Issued Apr. 6, 1993

[54] ELECTRONIC VIDEO DENTAL CAMERA

[75] Inventors: David H. Cooper, Saratoga; Charles S. Bush, Los Gatos, both of Calif.

[73] Assignee: Fuji Optical System Inc., Los Gatos, Calif.

Reexamination Request:
No. 90/002,036, Jun. 1, 1990

Reexamination Certificate for:
Patent No.: 4,727,416
Issued: Feb. 23, 1988
Appl. No.: 22,171
Filed: Mar. 5, 1987

[51] Int. Cl.⁵ .................. H04N 7/18; A61B 1/04; A61B 1/06
[52] U.S. Cl. .................. 358/98; 128/6; 358/229; 378/99; 433/29
[58] Field of Search .................. 358/98, 225, 229; 378/99; 433/29

[56] References Cited

U.S. PATENT DOCUMENTS

| | | |
|---|---|---|
| D. 267,745 | 1/1883 | Seeley . |
| D. 269,122 | 5/1983 | Seeley . |
| 3,051,166 | 8/1962 | Hovnanian . |
| 3,382,781 | 5/1968 | Hamilton . |
| 3,557,780 | 1/1971 | Sato .................. 128/4 |
| 3,622,785 | 11/1971 | Irwin et al. . |
| 3,884,222 | 5/1975 | Moore . |
| 3,903,877 | 9/1975 | Terada .................. 128/6 |
| 4,074,306 | 2/1978 | Kakinuma et al. .................. 128/6 |
| 4,260,376 | 4/1981 | Litel . |
| 4,273,535 | 6/1981 | Yamamoto . |
| 4,326,846 | 4/1982 | Sugai et al. . |
| 4,330,281 | 5/1982 | Hayashi . |
| 4,355,977 | 10/1982 | Ota et al. . |
| 4,369,768 | 1/1983 | Vukovic . |
| 4,385,344 | 5/1983 | Gonser .................. 362/804 |
| 4,390,028 | 6/1983 | Okano et al. . |
| 4,402,326 | 9/1983 | Okano et al. . |

(List continued on next page.)

FOREIGN PATENT DOCUMENTS

| | | |
|---|---|---|
| 3233410A1 | of 0000 | European Pat. Off. . |
| 0122537A1 | 10/1984 | European Pat. Off. . |
| 0184778A3 | 6/1986 | European Pat. Off. . |
| 296520 | 12/1988 | European Pat. Off. . |
| 2208902 | 8/1973 | Fed. Rep. of Germany . |
| 2308554 | 8/1974 | Fed. Rep. of Germany . |
| 2505798 | 8/1976 | Fed. Rep. of Germany . |
| 3045162 | 1/1982 | Fed. Rep. of Germany . |
| 53-45081 | 4/1978 | Japan . |
| 2183058 | of 0000 | United Kingdom . |
| 922994 | 4/1963 | United Kingdom . |

*Primary Examiner*—Howard W. Britton

[57] ABSTRACT

An electronic video dental camera is provided having a general shape of prior art dental mirrors, thereby being readily manipulated by dentists who are universally familiar with the manipulation of prior art dental mirrors. Such an electronic video dental camera includes a handle to be held the user, and a camera head located at the distal end of the handle, with the camera head being formed at an angle to the handle. One embodiment also includes a mirror so that the dental camera can be used simultaneously as both a video dental camera and a dental mirror. Another embodiment includes means to cause, as desired, the flow of a selected fluid over the camera lens in order to defog and/or clean the camera lens, thereby allowing proper viewing. In one embodiment, the camera head also includes light sources for properly illuminating the area to be viewed. As a feature of one embodiment, the handle includes means for transporting all appropriate signals and fluids to and from the camera head, and, if desired, valves and switching means located on the handle for controlling such communication to the camera head. In one embodiment, the handle is uniquely designed to have a one piece connector to connect to a cable from video monitor and control equipment, such connector providing communication with all elements connected to the camera head, such as power for a light source, video signals, fluids, etc.

U.S. PATENT DOCUMENTS

| | | |
|---|---|---|
| 4,425,599 | 1/1984 | Rieder et al. |
| 4,457,502 | 7/1984 | Beach |
| 4,468,197 | 8/1984 | Provost |
| 4,475,539 | 10/1984 | Konomura ............................ 128/6 |
| 4,479,499 | 10/1984 | Alfano |
| 4,491,865 | 1/1985 | Danna et al. |
| 4,492,574 | 1/1985 | Warrin et al. |
| 4,503,853 | 3/1985 | Ota et al. |
| 4,516,195 | 5/1985 | Gonser |
| 4,522,196 | 6/1985 | Cunningham et al. |
| 4,539,586 | 9/1985 | Danna et al. ............................ 128/6 |
| 4,568,283 | 2/1986 | Hotta et al. |
| 4,575,805 | 3/1986 | Moermann et al. |
| 4,593,699 | 6/1986 | Poncy |
| 4,601,284 | 7/1986 | Arakawa et al. |
| 4,608,622 | 8/1986 | Gonser |
| 4,621,618 | 11/1986 | Omagari |
| 4,629,425 | 12/1986 | Detsch |
| 4,638,353 | 1/1987 | Nagasaki et al. |
| 4,667,229 | 5/1987 | Cooper et al. |
| 4,684,018 | 8/1987 | Jarund |
| 4,727,416 | 2/1988 | Cooper et al. ......................... 358/98 |
| 4,744,752 | 5/1988 | Nakayama |
| 4,747,661 | 5/1988 | Ohkuwa |
| 4,759,347 | 7/1988 | Ando |
| 4,761,719 | 8/1988 | Yamada |
| 4,804,329 | 2/1989 | Nakayama et al. |
| 4,820,152 | 4/1989 | Warrin et al. |
| 4,826,431 | 5/1989 | Fujimura et al. |
| 4,836,782 | 6/1989 | Gonser |
| 4,849,859 | 7/1989 | Nagasawa |
| 4,850,868 | 7/1989 | Wright et al. |
| 4,858,001 | 8/1989 | Milbank et al. |
| 4,915,626 | 4/1990 | Lemmey |
| 4,940,411 | 7/1990 | Vassiliadis |

OTHER PUBLICATIONS

Fact Sheet on the American Dental Laser by American Dental Laser Incorporated of Birmingham, Mich.

Survey of Patients Treated with the American Dental Laser by American Dental Laser Incorporated of Birmingham, Mich.

Benefits of the American Dental Laser for the Dentist by American Dental Laser Incorporated of Birmingham, Mich.

Case Studies of Procedures with an American Dental Laser by American Dental Laser Incorporated of Birmingham, Mich.

The Revolutionary American Dental Laser of Birmingham, Mich.

"A short introduction to low level laser therapy," by Creative Medical Systems, Ltd. of the Netherlands.

Myers, "Dental Technology: Knocking at High-Tech's Door," *The Journal of the American Dental Association* (1989) 118:285–294.

Myers et al., "In vitro caries removal," *CDA Journal* (1988) pp. 9–10.

Myers et al., "First Soft Tissue Study Utilizing a Pulsed Nd:YAG Dental Laser" *Northwest Dentistry (1989) pp. 14–16.*

Myers et al., "What Lasers Can Do for Dentistry and You," *Dental Management* (1989) 29:26–30.

Dunlap, "Is There A Laser in Your Future," *Dental Economics* (1989).

*Laser Magazine,* NR. 1, Aug. (1989) Various articles and authors.

"Ultracompact CCD Color Television Camera", Y. Takemura et al., *Toshiba Review* No. 158, *Winter 1986.*

"A Review of Lasers in Dentistry", Terry D. Myers et al., published in the Italy scientific periodical Il Dentista Moderno, Jan. 1989.

"The use of a laser debridement of incipient caries", Terry D. Myers, *Journal of Prosthetic Dentistry,* vol. 53, No. 6.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 18-50:

In one embodiment of this invention, as shown in FIG. 3, a mirror 20 having a reflecting face 21 is placed such that the operator can use mirror 20 in much the same manner as prior art dental mirrors are used in order to visually see the viewed image which is simultaneously being received by camera head 14. While FIG. 3 shows one embodiment of mirror 20 which is [a] placed in a groove 19 inside of camera head [15] *14*, in another embodiment (not shown) mirror 20 is affixed to opposite sides to camera head 14. In the embodiment shown FIG. 3, mirror *20* is held in a slot having a circular cross section within camera head [15] *14* in an interference fit, and thus angle B is adjustable. To allow for such adjustment, the opening into camera head 14 is wider than the thickness of mirror 20. Mirror 20 is placed at an angle B to the viewed image. A wide range of camera head to viewed image angle A and mirror to viewed image angle B can be used in accordance with the teachings of this invention, however it has been found that an angle A of approximately 45° is roughly equivalent to typical prior art dental mirrors. Similarly, a dental mirror angle B of approximately 45° is suitable for most uses. However, angles A and B can vary widely, and there is no required relationships between angles A and B, so long as the dental camera and mirror 20 function in [an] *a* convenient manner for the operator. In fact, angle A can range from 0° to 180°, and angle B can range from 0° to 180° without detracting from the spirit of this invention. Furthermore, it *is* possible that camera head 14 be inverted such that face 15 is located on the bottom of FIG. 3, with of course a different location for the viewed image. In another embodiment of this invention, a face of camera head 14 is itself used as a mirror.

AS A RESULT OF REEXAMINATION, IT HAS BEEN DETERMINED THAT:

Claims 15, 19, 21-24 and 27 are cancelled.

Claims 1, 6, 14, 20 and 25 are determined to be patentable as amended.

Claims 2-5, 7-13, 16-18, 26 and 28, dependent on an amended claim, are determined to be patentable.

New claims 29-76 are added and determined to be patentable.

1. A dental camera for use in displaying an image from inside the mouth onto a monitor comprising an electronic video endoscope having a shape like a dental mirror, said endoscope comprising:

a handle *having a longitudinal axis, a proximal end, and a distal end;* a camera head *for placement within the mouth* including a camera lens, said camera head located at [the] *said* distal end of said handle, said camera head being formed such that said camera lens is placed at an angle from the axis of said handle, *wherein said camera lens is located in said camera head such that said image is directed to said camera lens without reflection by a planar mirrored surface, and wherein one or both of said camera head and said camera lens is reflexed toward said handle for retroflexed viewing;* [and]

means for providing a flow of fluid over the surface of said camera lens;

*means for connecting one or more cables to said handle at or near said proximal end; and*

*means interior to said handle for providing communication between said one or more cables and said camera head.*

6. A dental camera as in claim [1] *66* wherein said handle comprises means interior to said handle, for communication with said camera head.

14. A dental camera for use in displaying an image from inside the mouth onto a monitor comprising an electronic video endoscope having a shape like a dental mirror, said endoscope comprising:

a handle *having a longitudinal axis, a proximal end, and a disial end;* and a camera head *for placement within the mouth* including a camera lens, said camera head located at the distal end of said handle, said camera head being formed such that said camera lens is placed at an angle from the axis of said handle, *and wherein one or both of said camera head and said camera lens is reflexed toward said handle for retroflexed viewing;* wherein said camera head includes means for providing light, *said means for providing light including one or more fiber optic light guides bringing illumination from a light source and including a curvature such that said illumination is routed to* [and] a lens *to be emitted from the same face of said camera head as receives said image,* such that the light from said means for providing light is dispersed toward the area being viewed by said camera head;

*means for connecting one or more cables to said handle at or near said proximal end; and*

*means interior to said handle for providing communication between said one or more cables and said camera head.*

20. A dental camera as in claim 19 wherein said fiber optic light guide includes a bend [within the range of 0°-180°] *of approximately 135°*.

25. A dental camera for use in displaying an image from inside the mouth onto a monitor comprising an electronic video endoscope having a shape like a dental mirror, said endoscope comprising:

a handle;

a camera head *for placement within the mouth* including a camera lens, said camera head located at the distal end of said handle, said camera head being formed such that said camera lens is placed at an angle from the axis of said handle, *wherein said camera lens is located in said camera head such that* said image is directed to said camera lens without reflection by a planar mirrored surface;

means for connecting one or more cables to said handle at or near said proximal end;

means interior to said handle for providing communication between said one or more cables and said camera head; and an imaging [means] device located external to said camera head.

29. A dental camera as in claim 1 wherein said camera head further comprises an illumination port for providing illumination to the area being viewed by said camera lens.

30. A dental ccamera as in claim 29 wherein the illumination from said illumination port is emitted from the same face of said camera head as receives said image.

31. A dental camera as in claim 29 wherein said illumination port comprises a lens.

32. A dental camera as in claim 30 wherein said illumination port comprises a lens.

33. A dental camera as in claim 29 which further includes one or more color filters in the path between said illumination port and an image being viewed.

34. A dental camera as in claim 33 wherein said color filter is an infrared filter.

35. A dental camera as in claim 10 wherein said imaging device is located within said camera head such that said image is directed to said imaging device from said camera lens without reflection by a planar mirror.

36. A dental camera as in claim 10 wherein said camera head further comprises an illumination port for providing illumination to the area being viewed by said camera lens.

37. A dental camera as in claim 36 wherein the illumination from said illumination port is emitted from the same face of said camera head as receives said image.

38. A dental camera as in claim 36 wherein said illumination port comprises a lens.

39. A dental camera as in claim 37 wherein said illumination port comprises a lens.

40. A dental camera as in claim 10 which includes a malleable member connecting said handle and said camera head.

41. A dental camera as in claim 10 which further includes one or more color filters in the path between said means for providing light and an image being viewed.

42. A dental camera as in claim 41 wherein said color filter is an infrared filter.

43. A dental camera as in claim 14 wherein said camera head comprises an imaging device.

44. A dental camera as in claim 14 wherein said imaging device is located within said camera head such that said image is directed to said imaging device from said camera lens without reflection by a planar mirror.

45. A dental camera as in claim 14 wherein said camera head further comprises an illumination port for providing illumination to the area being viewed by said camera lens.

46. A dental camera as in claim 45 wherein the illumination from said illumination port is emitted from the same face of said camera head as receives said image.

47. A dental camera as in claim 45 wherein said illumination port comprises a lens.

48. A dental camera as in claim 46 wherein said illumination port comprises a lens.

49. A dental camera as in claim 14 wherein said camera lens is located in said camera head such that said image is directed to said camera lens without reflection by a planar mirrored surface.

50. A dental camera as in claim 25 wherein said camera head is reflexed towards said handle for retroflexed viewing.

51. A dental camera as in claim 25 wherein said camera lens is reflexed towards said handle for retroflexed viewing.

52. A dental camera as in claim 25 which further comprises an imaging device located such that said image is directed to said imaging device from said camera lens without reflection by a planar mirror.

53. A dental camera as in claim 25 wherein said camera head further comprises an illumination port lens for providing illumination to the area being viewed by said camera lens.

54. A dental camera as in claim 53 wherein the illumination from said illumination port is emitted from the same face of said camera head as receives said image.

55. A dental camera as in claim 53 wherein said illumination port comprises a lens.

56. A dental camera as in claim 54 wherein said illumination port comprises a lens.

57. A dental camera as in claim 53 which further includes one or more color filters in the path between said illumination port and an image being viewed.

58. A dental camera as in claim 57 wherein said color filter is an infrared filter.

59. A dental camera for use in displaying an image from inside the mouth onto a monitor comprising an electronic video endoscope having a shape like a dental mirror, said endoscope comprising:

a handle;

a camera head for placement within the mouth including a camera lens, said camera head located at the distal end of said handle, said camera head being formed such that said camera lens is placed at an angle from the axis of said handle, wherein said camera lens is located in said camera head such that said image is directed to said camera lens without reflection by a planar mirrored surface;

means for providing a flow of fluid over the surface of said camera lens; and a malleable member connecting said handle and said camera head.

60. A dental camera for use in displaying an image from inside the mouth onto a monitor comprising an electronic video endoscope having a shape like a dental mirror, said endoscope comprising:

a handle; and a camera head for placement within the mouth including a camera lens, said camera head located at the distal end of said handle, said camera head being formed such that said camera lens is placed at an angle from the axis of said handle;

wherein said camera head includes means for providing light and a lens such that the light from said means for providing light is dispersed toward the area being viewed by said camera head; and a malleable member connecting said handle and said camera head.

61. A dental camera for use in displaying an image from inside the mouth onto a monitor comprising an electronic video endoscope having a shape like a dental mirror, said endoscope comprising:

a handle; and a camera head for placement within the mouth including a camera lens, said camera head located at the distal end of said handle, said camera head being formed such that said camera lens is placed at an angle from the axis of said handle;

wherein said camera head includes means for providing light and a lens such that the light from said means for providing light is dispersed toward the area being viewed by said camera head; and one or more color filters in the path between said means for providing light and an image being viewed.

62. A dental camera as in claim 61 wherein said color filter is an infrared filter.

63. A dental camera for use in displaying an image from inside the mouth onto a monitor comprising an electronic video endoscope having a shape like a dental mirror, said endoscope comprising:

a handle; and a camera head for placement within the mouth including a camera lens, said camera head located at the distal end of said handle, said camera head being formed such that said camera lens is placed at an angle from the axis of said handle; and means for providing light comprising a fiber optic light guide including a bend of approximately 135° bringing illumination from a light source to a lens such that the light is dispersed toward the area being viewed by said camera head.

64. A dental camera for use in displaying an image from inside the mouth onto a monitor comprising an electronic video endoscope having a shape like a dental mirror, said endoscope comprising:

a handle;

a camera head for placement within the mouth including a camera lens, said camera head located at the distal end of said handle, said camera head being formed such that said camera lens is placed at an angle from the axis of said handle;

an imaging device; and a color filter in the image path between the image being viewed and said imaging device.

65. A dental camera as in claim 64 wherein said color filter is an infrared filter.

66. A dental camera as in claim 64 which includes a malleable member connecting said handle and said camera head.

67. A dental camera for use in displaying an image from inside the mouth onto a monitor comprising an electronic video endoscope having a shape like a dental mirror, said endoscope comprising:

a handle;

a camera head for placement within the mouth including a camera lens, said camera head located at the distal end of said handle, said camera head being formed such that said camera lens is placed at an angle from said axis of said handle, wherein said camera lens is located in said camera head such that said image is directed to said camera lens without reflection by a planar mirrored surface; and an imaging means located external to said camera head and within said handle.

68. A dental camera for use in displaying an image from inside the mouth onto a monitor comprising an electronic video endoscope having a shape like a dental mirror, said endoscope comprising:

a handle;

a camera head for placement within the mouth including a camera lens, said camera head located at the distal end of said handle, said camera head being formed such that said camera lens is placed at an angle from said axis of said handle, wherein said camera lens is located in said camera head such that said image is directed to said camera lens without reflection by a planar mirrored surface;

an imaging means located external to said camera head and within said handle; and a malleable member connecting said handle and said camera head.

69. A dental camera for use in displaying an image from inside the mouth onto a monitor comprising an electronic video endoscope having a shape like a dental mirror, said endoscope comprising:

a handle;

a camera head for placement within the mouth including a camera lens, said camera head located at the distal end of said handle, said camera head being formed such that said camera lens is placed at an angle from the axis of said handle, wherein said camera lens is located in said camera head such that said image is directed to said camera lens without reflection by a planar mirrored surface; and an imaging device located external to said camera head such that image is directed to said imaging device from said camera lens without reflection by a planar mirror.

70. A dental camera for use in displaying an image from inside the mouth onto a monitor comprising an electronic video endoscope having a shape like a dental mirror, said endoscope comprising:

a handle;

a camera head for placement within the mouth including a camera lens, said camera head located at the distal end of said handle, said camera head being formed such that said camera lens is placed at an angle from the axis of said handle, wherein said camera lens is located in said camera head such that said image is directed to said camera lens without reflection by a planar mirrored surface;

an imaging means located external to said camera head;

an illumination port for providing illumination to the area being viewed by the area being viewed by said camera lens; and one or more color filters in the path between said illumination port and an image being viewed.

71. A dental camera as in claim 70 wherein said one or more color filters comprise an infrared filter.

72. A dental camera for use in displaying an image from inside the mouth onto a monitor comprising an electronic video endoscope having a shape like a dental mirror, said endoscope comprising:

a handle;

a camera head for placement within the mouth including a camera lens, said camera head located at the distal end of said handle, said camera head being formed such that said camera lens is placed at an angle from the axis of said handle, wherein said camera lens is located in said camera head such that said image is directed to said camera lens without reflection by a planar mirrored surface;

means for providing a flow of fluid over the surface of said camera lens;

an illumination port for providing illumination to the area being viewed by said camera lens; and one or more color filters in the path between said illumination port and an image being viewed.

73. A dental camera as in claim 72 wherein said one or more color filters comprise an infrared filter.

74. A dental camera for use in displaying an image from inside the mouth onto a monitor comprising an electronic video endoscope having a shape like a dental mirror, said endoscope comprising:

a handle;

a camera head for placement within the mouth including a camera lens, said camera head located at the distal end of said handle, said camera head being formed such that said camera lens is placed at an angle from the axis of said handle, wherein said camera lens is located in said camera head such that said image is directed to said camera lens without reflection by a planar mirrored surface;

means for providing a flow of fluid over the surface of said camera lens; and a malleable member connecting said handle and said camera head.

75. A dental camera as in claim 74 which further includes one or more color filters in the path between said means for providing light and an image being viewed.

76. A dental camera as in claim 75 wherein said one or more color filters comprise an infrared filter.

* * * * *